United States Patent [19]

Salvador et al.

[11] Patent Number: 5,436,273

[45] Date of Patent: Jul. 25, 1995

[54] PSYCHOACTIVE PROPARGYLAMINE DERIVATIVES USED IN THE TREATMENT OF ANXIETY, PSYCHOTIC STATES OR AGGRESSION

[75] Inventors: Romano Salvador, Laval; David Z. Simon; Louis Leonard, both of Montreal, all of Canada

[73] Assignee: Lowchol Scientific, Inc., Frelighsburg, Canada

[21] Appl. No.: 157,453

[22] Filed: Nov. 26, 1993

Related U.S. Application Data

[63] Continuation of Ser. No. 891,499, May 29, 1992, abandoned.

[51] Int. Cl.$^6$ .................. A61K 31/13; A61K 31/47; A61K 31/445; A61K 31/425
[52] U.S. Cl. .................. 514/671; 514/315; 514/317; 514/351; 514/367; 514/461; 514/646; 514/625
[58] Field of Search ............... 514/646, 367, 315, 317, 514/461, 351, 625, 671

[56] References Cited

FOREIGN PATENT DOCUMENTS 1927528 12/1970 Germany.
918217 2/1963 United Kingdom.
1055548 1/1967 United Kingdom.
1304026 1/1973 United Kingdom.

OTHER PUBLICATIONS

M. M. Kwatra et al., Journal of Medicinal Chemistry, vol. 21, No. 3, 1978, pp. 253–257.
D. Z. Simon et al., Journal of Medicinal Chemistry, vol. 13, No. 6, 1970, pp. 1249–1250.
S. Lipper et al., Psychopharmacology, vol. 62, No. 2, 1979, pp. 123–128.
J. O. Cole, Medical Clinics of North America, vol. 72, 1988, pp. 815–830.
Medline Abstracts, Accession No. 90081512 & Med. J. Aust. 1989, 151(11–12), pp. 697–701 (abstract enclosed).
Medlin Abstracts, Accession No. 88086954 & J. Clin. Psychiatry 1987, vol. 48, Suppl., pp. 7–11 (abstract enclosed).
Medline Abstracts, Accession No. 84239636 & J. Clin. Psychiatry, 1984, vol. 45, No. 7, pp. 70–77, (abstract enclosed).
Y. C. Martin et al, Journal of Medicinal Chemistry (1975), vol. 18 (#9) pp. 883–888.
Journal of Medicinal Chemistry, 1978, vol. 21, No. 3, pp. 253–257, Kwatra, Madan, Simon, D. Salvador, R. and Cooper, L.

*Primary Examiner*—Raymond Henley, III
*Assistant Examiner*—T. J. Criares
*Attorney, Agent, or Firm*—Phillips Moore Lempio & Finley

[57] ABSTRACT

Propargylamine derivatives having the general formula:

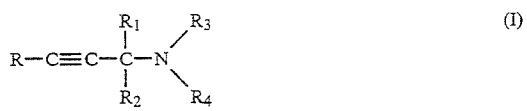

wherein R is a hydrogen atom, an unsubstituted phenyl group or a phenyl group substituted with halogen, trifluoromethyl, loweralkoxy, nitro, cyano, amido or N,N-diloweralkylamido, $R_1$, $R_2$ or $R_3$ are the same or different and each represent a hydrogen atom or a loweralkyl group, $R_4$ is a hydrogen atom or a loweralkyl, benzyl, phenethyl or furyl group, or $R_3$ and $R_4$ together with the nitrogen atom to which they are attached form a piperidinyl group, and their pharmaceutically acceptable acid addition salts, have been found to be useful in the treatment of anxiety, psychotic states and aggressive behavior in affected animals.

13 Claims, 1 Drawing Sheet

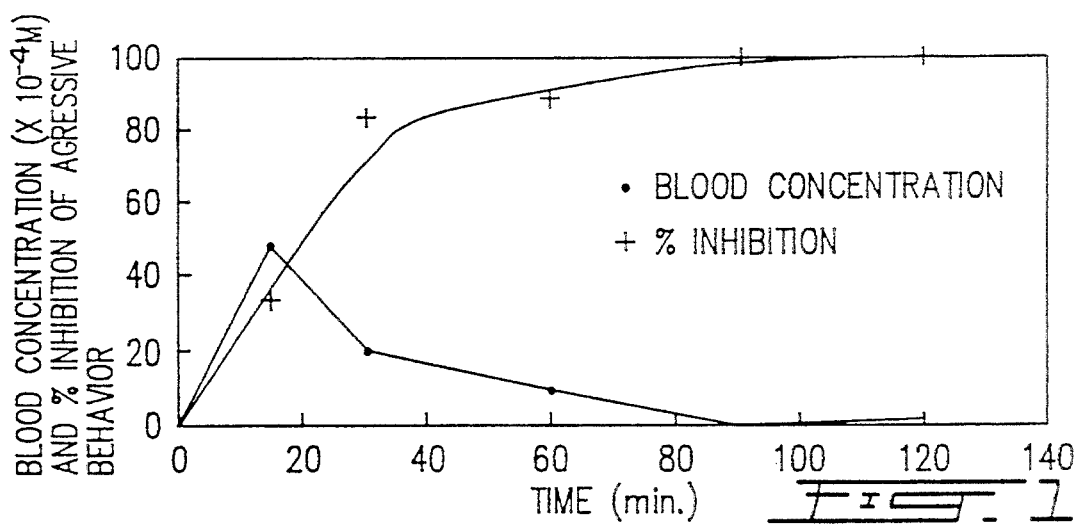
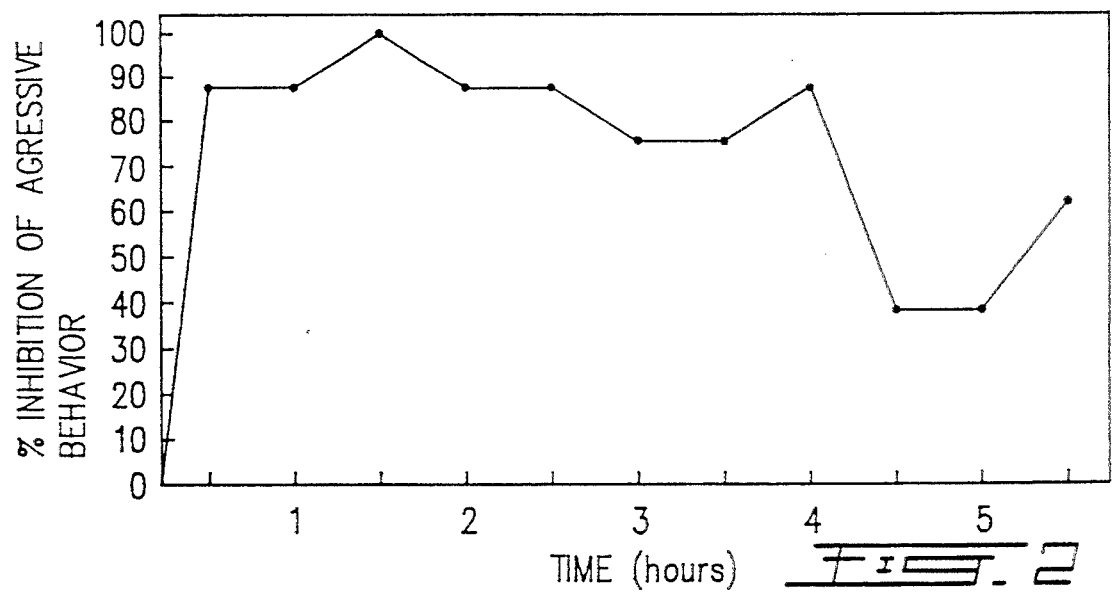
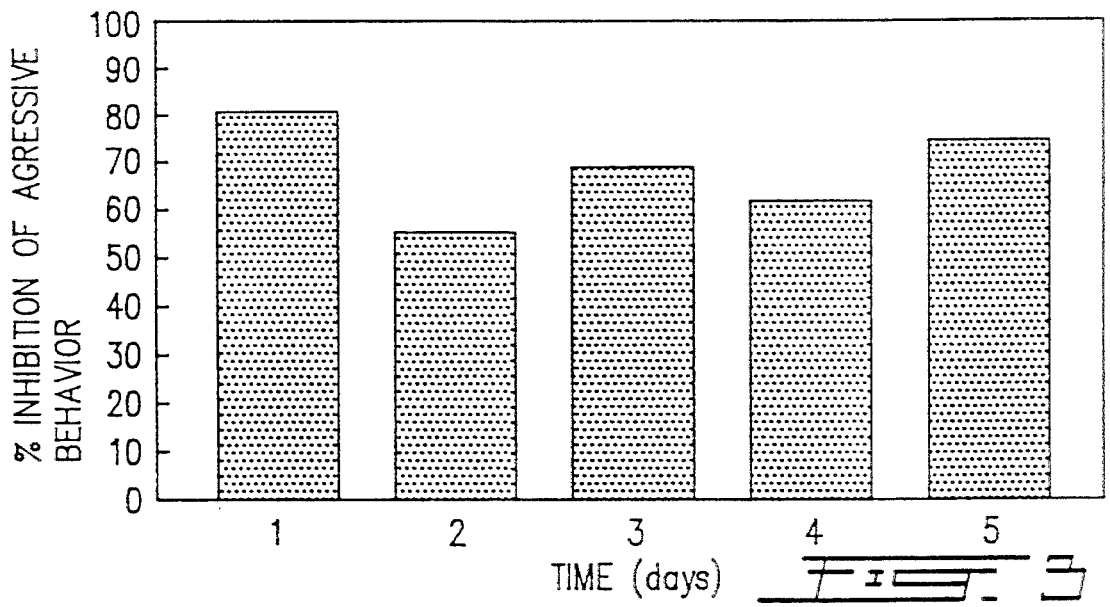

PSYCHOACTIVE PROPARGYLAMINE DERIVATIVES USED IN THE TREATMENT OF ANXIETY, PSYCHOTIC STATES OR AGGRESSION

This application is a continuation of application Ser. No. 07/891,499, filed May 29, 1992, now abandoned.

BACKGROUND OF THE INVENTION

The present invention relates to pharmacologically active derivatives of propargylamine and their use in the treatment of anxiety, psychotic states and aggressive behavior in affected animals.

Aggressive behavior as well as anxiety appear to be adaptation factors. However, when they become excessive or pathologic, they disable the normal interaction of an individual within society. It then becomes necessary to inhibit these behaviors.

Antipsychotic and anxiolytic agents such as chlorpromazine and diazepam are widely used to treat such pathologic anxiety and/or aggresivity. However, when used in the appropriate doses, these agents cause undesirable side effects such as sedation and ataxia. Buspirone, a well known anxiolytic agent, causes markedly less sedation than diazepam, but its anxiolytic activity is initiated only several days after administration. The discovery of new anxiolytic agents that do not induce undesirable side effects and have a more rapid onset of action would be a valuable addition to the present psychotherapeutic agents available to the physician.

SUMMARY OF THE INVENTION

Applicants have found quite unexpectedly that a group of propargylamine derivatives having the general formula:

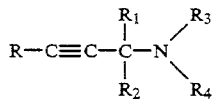

wherein:
- R is a hydrogen atom, an unsubstituted phenyl group or a phenyl group substituted with halogen, trifluoromethyl, loweralkoxy, nitro, cyano, amido or N,N-diloweralkylamido;
- $R_1$, $R_2$ or $R_3$ are the same or different and each represent a hydrogen atom or a loweralkyl group; and
- $R_4$ is a hydrogen atom or a loweralkyl, benzyl, phenethyl or furyl group; or
- $R_3$ and $R_4$ together with the nitrogen atom to which they are attached form a piperidinyl group; and their pharmaceutically acceptable acid addition salts, are useful in the treatment of anxiety and psychotic states, and have an enhanced antiaggressive activity with minimal sedation effect and no impairment of motor activity. In contrast to buspirone, the pharmacological activity of the derivatives of formula (I) is initiated within approximately 30 minutes after administration.

Accordingly, the present invention provides a pharmaceutical composition for the treatment of anxiety, psychotic states and aggressive behavior in an affected animal, comprising a non-toxic effective amount of a propargylamine derivative of formula (I) as defined above, or a pharmaceutically acceptable acid addition salt thereof, together with a pharmaceutically acceptable carrier therefor.

The invention also provides, in another aspect thereof, a method of treating anxiety, psychotic states and aggressive behavior in an affected animal, which comprises administering to such a human a non-toxic effective dose of a propargylamine derivative of formula (I) as defined above, or a pharmaceutically acceptable acid addition salt thereof.

DESCRIPTION OF PREFERRED EMBODIMENTS

The preparation of derivatives of formula (I) in which R is hydrogen has been disclosed in British patent No. 1,304,026. Such derivatives are described in this patent as being valuable intermediates in the production of plant protection agents and pharmaceuticals.

The synthesis and pharmacology of some derivatives of formula (I) in which R is an unsubstituted or substituted phenyl group have been reported in Journal of Medicinal Chemistry, 1970, Vol. 13, N° 6, pages 1249–1250 and in Journal of Medicinal Chemistry, 1978, Vol. 21, N° 3, pages 253–257. Certain compounds are described as possessing some monoamine oxidase (MAO) inhibitory, anorexigenic and blood lipid lowering activity, while other compounds show tryptamine-like behavioral effects in mice.

However, as far as is known, no anxiolytic, antipsychotic and antiaggressive activities have ever been attributed to these known compounds.

Particularly preferred compounds for use in the treatment of anxiety, psychotic states and aggressive behavior are the 3-aryl propargylamine derivatives of formula (Ia):

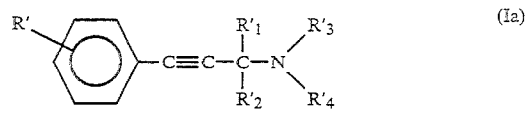

wherein R' is in the meta or para position and represents a hydrogen or halogen atom, a trifluoromethyl, loweralkoxy, nitro, cyano, amido or N,N-diloweralkylamido group, $R'_1$ is a hydrogen atom, $R'_2$ and $R'_3$ are the same or different and each represent a hydrogen atom or a loweralkyl group, $R'_4$ is a hydrogen atom or a loweralkyl, benzyl, phenethyl or furyl group, or $R'_3$ and $R'_4$ together with the nitrogen atom to which they are attached form a piperidinyl group, and their pharmaceutically acceptable acid addition salts. Preferably, R' is hydrogen, para-chloro, meta-trifluoromethyl, para-methoxy, para-nitro, para-cyano, para-amido or para-N,N-dimethylamido, $R'_1$ is hydrogen, $R'_2$ and $R'_3$ are the same or different and each represent a hydrogen atom or a methyl, ethyl or propyl group, $R'_4$ is a hydrogen atom or a methyl, ethyl, benzyl, phenethyl or 2-furyl group, or $R_3$ and $R_4$ together with the nitrogen atom to which they are attached form a piperidinyl group.

Among the derivatives of formula (I) in which R is a hydrogen atom, those of the formula (Ib):

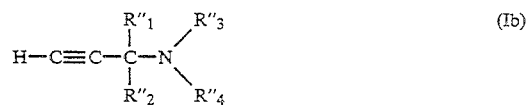

wherein R″₁ is a hydrogen atom or a loweralkyl group, R″₂ is a loweralkyl group, R″₃ and R″₄ are the same or different and each represent a hydrogen atom or a loweralkyl group, are preferred. The compound of formula (Ib) in which R″₂ is a methyl radical and R″₁, R″₃ and R″₄ each represent a hydrogen atom is particularly noteworthy for its enhanced anti-aggressive activity, very low toxicity and non-sedative effect.

As used herein, the term "loweralkyl" or "loweralkoxy" means straight or branched alkyl or alkoxy of 1 to 6 carbon atoms. Preferred compounds are those where the lower alkyl or alkoxy group has 1 to 4 carbon atoms, with methyl, ethyl, propyl, methoxy, ethoxy and propoxy being particularly preferred.

In addition to the synthesis methods described in the aforementioned publications, the 3-aryl propargylamine derivatives of formula (Ia) can be prepared according to the following reaction scheme I:

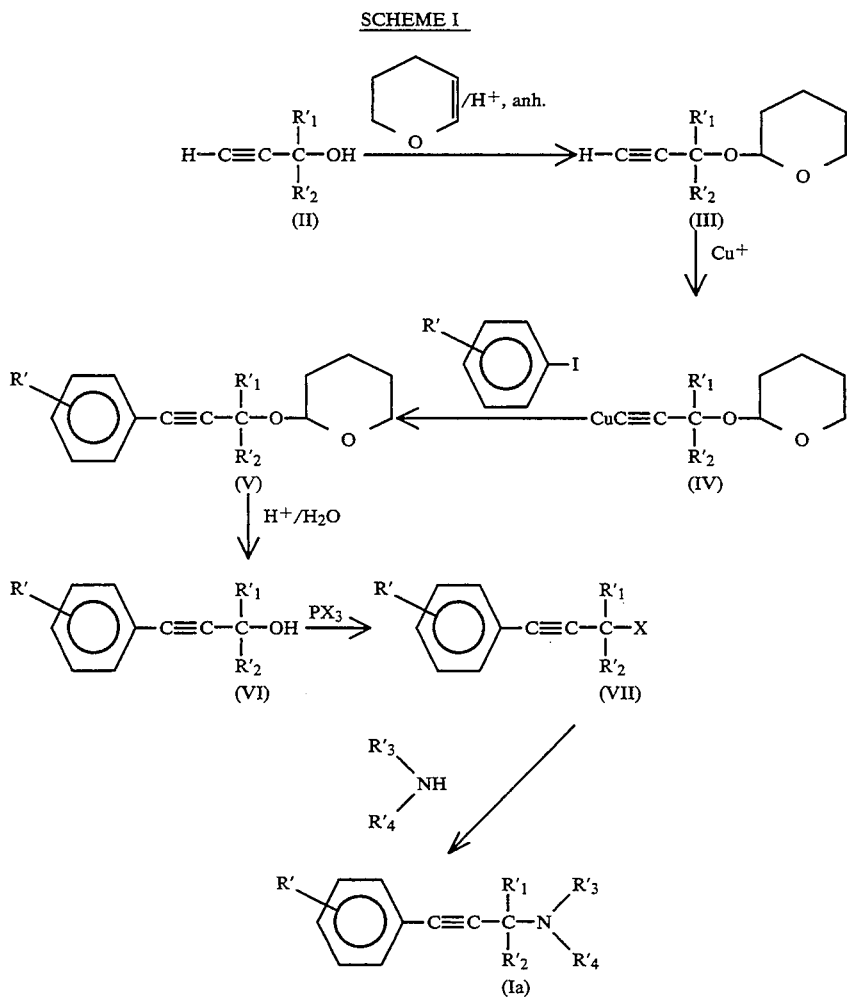

In this method, the alcohol of formula (II) is first converted to the tetrahydropyranyloxy derivative of formula (III) which is then converted to its copper (I) salt of formula (IV). The copper acetylenide of formula (IV) is reacted with a selected p-iodoaryl moiety to give the arylacetylenic derivative of formula (V). The compound of formula (V) is then hydrolysed to the alcohol of formula (VI) which is thereafter transformed to the halide derivative of formula (VII) by reaction with PX₃ in which X is halogen atom. Aminolysis of the compound of formula (VII) yields the desired 3-aryl propargylamine derivative of formula (Ia).

It is also possible to prepare the primary amine derivatives of formula (Ia) in which R′₃ and R′₄ each represent a hydrogen atom according to the following reaction scheme II:

SCHEME II

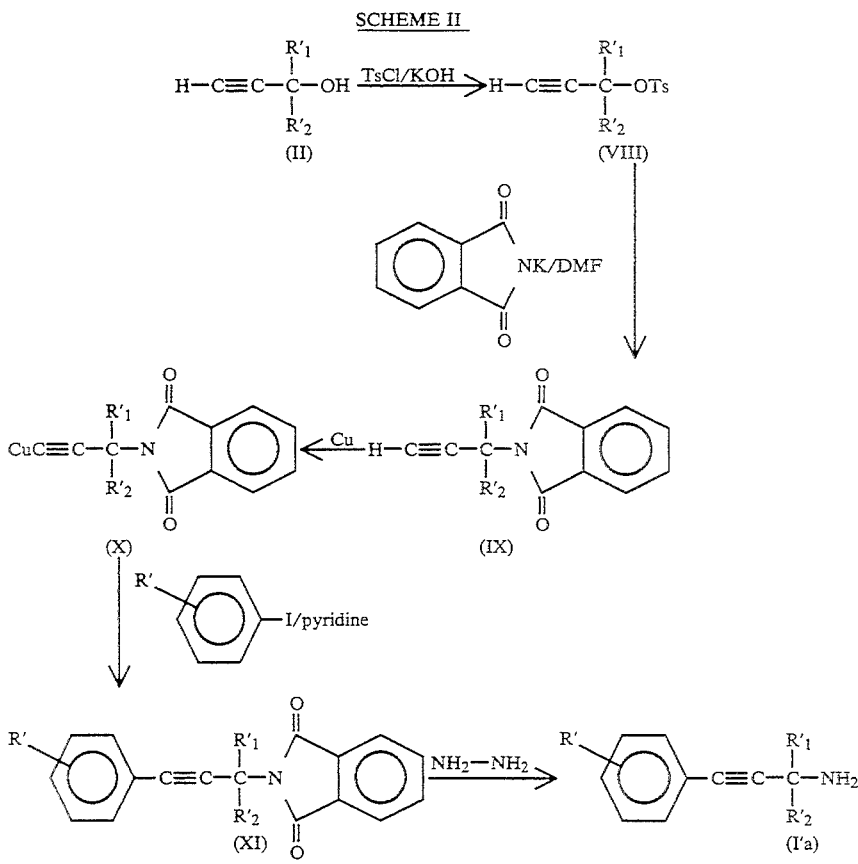

In this method, the alcohol of formula (II) is converted to the tosyloxy derivative of formula (VIII) which is then converted to the phthalimido derivative of formula (IX). The compound of formula (IX) is converted to its copper (I) salt of formula (X) which is reacted with a selected p-iodoaryl moiety to yield the arylphthalimido alkynyl derivative of formula (XI). The latter is then reacted with hydrazine to give the desired primary amine of formula (I'a).

The primary amine derivatives of formula (Ib) in which $R''_3$ and $R''_4$ each represent a hydrogen atom can be prepared according to the following reaction scheme III:

SCHEME III

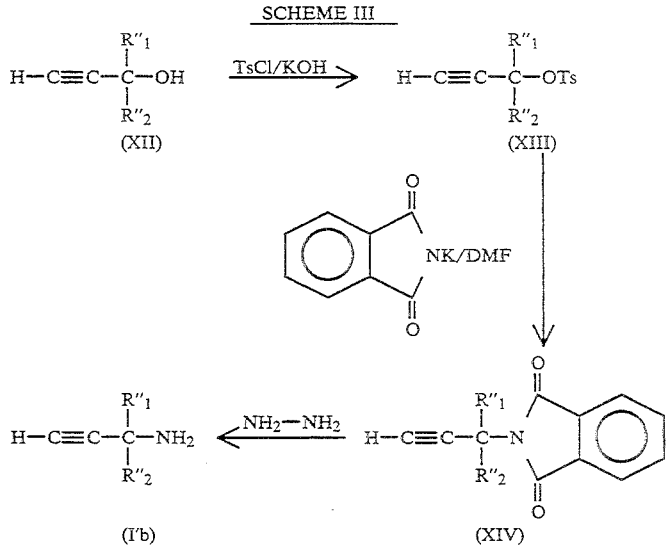

In this method, the alcohol of formula (XII) is first transformed into its tosyloxy derivative of formula (XIII) which is then converted to the phthalimido derivative of formula (XIV). The phthalimido derivative of formula (XIV) is thereafter converted to the desired primary amine of formula (I'b) by using hydrazine or any other suitable cleavage agent.

The N-substituted propargylamine derivatives of formulae (Ia) and (Ib) can be obtained by alkylation of the primary amines of formulae (I'a) and (I'b) or by amination their corresponding halide or tosyloxy derivatives with a selected amine.

As noted above, the compounds of formula (I) and particularly those of formulae (Ia) and (Ib) have been found to be useful in the treatment of anxiety, psychotic states and aggressive behavior. They can be administered in either their free base or salt form. Examples of suitable pharmaceutically acceptable acid addition salts of the propargylamine derivatives of formula (I) are salts of the amine with a pharmaceutically acceptable acid such as hydrochloric acid, sulfuric acid, fumaric acid, citric acid, maleic acid, oxalic acid, tartaric acid, and the like.

The pharmacologically active compounds of the invention can be processed in accordance with conventional methods of pharmaceutical technology to produce medicinal agents for administration to patients. They can be employed in admixture with conventional excipients, i.e., pharmaceutically acceptable organic or inorganic carrier substances suitable for parenteral or enteral (e.g. oral) application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

For parenteral application, particularly suitable are injectable, sterile solutions, preferably oily or aqueous solutions, as well as suspensions and emulsions. Ampoules are convenient unit dosages.

For enteral application, particularly suitable are uncoated or sugar-coated tablets, liquids, drops, suppositories, or capsules. A syrup, elixir or the like can be used wherein a sweetened vehicle is employed.

Where use is made of 2-amino-3-butyne in free base form, which is a compound of formula (Ib) in which $R''_2$ is a methyl radical and $R''_1$, $R''_3$ and $R''_4$ are each a hydrogen atom, and which has a high vapor pressure at room temperature, such a compound can be utilized in inhalant therapy and thus be administered by intrapulmonary route.

Generally, the compounds of formula (I) are dispensed in unit dosage form comprising about 30 to about 500 mg in a pharmaceutically acceptable carrier per unit dose. The daily dose is preferably less than about 200 mg, but doses as high as 3000 mg per day may be employed in exceptional cases.

The compounds of formula (I) can also be used for the preventive treatment of animals such as cows, pigs, etc., which injure each other while being shipped to market.

Further features and advantages of the invention will become more readily apparent from the following non-limiting examples illustrating the synthesis of compounds of the invention, and description of pharmacological trials which have been performed with a view to determining their various properties which render them useful in the treatment of anxiety, psychotic states and aggressive behavior.

BRIEF DESCRIPTION OF THE DRAWINGS

In the accompanying drawings:

FIG. 1 graphically illustrates the time dependent blood concentration of 2-amino-3-butyne and the inhibition of aggressive behavior in combative mice;

FIG. 2 graphically illustrates the duration of the inhibitory effect that 2-amino-3-butyne has on the aggressive behavior of combative mice after administration of a single dose (10 mg/kg i.p.); and FIG. 3 graphically illustrates the persistence of the inhibitory effect that 2-amino-3-butyne has on the aggressive behavior of combative mice after repeated daily administration of 10 mg/kg i.p.

EXAMPLE 1

2-Amino-4-(p-chlorophenyl)-3-butyne (formula (Ia) with $R'=p$-Cl, $R'_1=R'_3=R'_4=H$, $R'_2=CH_3$ a) Tetrahydropyranyloxy-3-butyne 3-Butyn-2-ol (1 mol) and dihydropyran (1.1 mol) are mixed and 2 drops of concentrated hydrochloric acid are added. The reaction mixture is allowed to stand 2 to 3 hours at room temperature and a few pellets of sodium hydroxide are added. After filtration, the product is distilled.

(b.p. 74°–6° C./15 mm; yield 80%)

b) Copper (I)-2-tetrahydropyranyloxy-3-butynide

Copper sulfate pentahydrate (0.1 mol) and 28% ammonium hydroxide (100 ml) are stirred under nitrogen for 5 minutes and water (300 ml) is added. After 5 minutes of stirring, hydroxylamine hydrochloride (0.2 mol) is added and the reaction mixture stirred for 5–10 minutes. The THP ether, prepared in step (a) above (0.1 mol) in ethanol (300 ml), is then added. The solution is added to a litre of water containing 70 ml of glacial acetic acid. The yellow precipitate produced is filtered, washed with water and dried in a rotary evaporator at room temperature for 3 days. No further purification is done on this intermediate.

c) 2-Tetrahydropyranyloxy-4-(p-chlorophenyl)-3-butyne

The crude copper (I) salt prepared in step (b) above (0.1 mol) is mixed under nitrogen with dry pyridine (300 ml). p-Chloroiodo benzene (0.1 mol) in dry pyridine (30 ml) is added and the reaction mixture is refluxed, under nitrogen, for 15 hours. The reaction mixture is cooled to room temperature and poured into 500 ml water. The whole is allowed to stand for 2–3 hours. The upper layer is decanted and the precipitate is extracted with ether. The ether is washed and dried. The ether is evaporated end the resulting oil is distilled to give 2-tetrahydropyranyloxy-4-(p-chlorophenyl)-3-butyne.

(b.p. 114°–16° C./0.2 mm; yield 80%)

d) 2-Hydroxy-4-(p-chlorophenyl)-3-butyne

The product prepared in step (c) above (0.05 mol) and p-toluenesulphonic acid (1 g) dissolved in ethanol (50 ml) is refluxed for 3 hours. After cooling, 2 to 3 g potassium carbonate is added and the mixture is filtered. The ethanol is removed in vacuo and the residue is taken up in ether/water (40 ml/10 ml). The ether layer is washed, dried and the ether is removed in vacuo. The residue is distilled to afford the title compound in almost quantitative yield.

(b.p. 85°–6° C., m.p. 71°–72° C.; yield 95%)

e) 2-Bromo-4-(p-chlorophenyl)-3-butyne

The product prepared in step (d) above (0.05 mol) and dry pyridine (1 ml) are dissolved in dry ether (20 ml) and cooled to 0° C. Phosphorous tribromide (0.025 mol) in 20 ml dry ether is added dropwise with stirring. The reaction mixture is then refluxed for 3 hours. After cooling the mixture to 0°, the excess PBr$_3$ is destroyed by adding crushed ice. The ether layer is washed and dried. The ether is removed and the title product is obtained by distillation.

(b.p. 71°–72° C./0.2 mm; yield 70%)

f) 2-Amino-4-(p-chlorophenyl)-3-butyne hydrochloride

The product prepared in step (e) above is added, with stirring, to 5 to 10 times excess of ammonia. The mixture is stirred at room temperature for 3 hours. An excess of ether is then added and the precipitate is filtered off. The ether is removed in vacuo and the resulting oil is used directly to prepare the hydrochloride salt.

The hydrochloride salt is prepared by adding ethereal hydrogen chloride to an ether solution of the free base.

(m.p. 230° dec.; yield 60%)

EXAMPLE 2

2-Amino-4-(p-cyanophenyl)-3-butyne (formula (Ia) with R'=p-CN, R'$_1$=R'$_3$=R'$_4$=H, R'$_2$=CH$_3$)

a) 2-Tosyloxy-3-butyne

To a solution of tosyl chloride (0.5 mole) and commercial 3-butyn-2-ol (0.4 mole; 40–50% aqueous solution) in ether (350 ml), potassium hydroxide (2.5 moles) is slowly added over a period of 15–30 minutes. The temperature is maintained at 0°–5° C. for the entire period and the reaction mixture is allowed to stand for 90 minutes. When the reaction is complete, the ether phase is washed and dried. Removal of the ether, in vacuo, yields crude 2-tosyloxy-3-butyne.

(m.p. 49°–51° C.; yield 95%).

b) 2-Phthalimido-3-butyne

To a solution of potassium phthalimide (0.275 mole) in DMF (20 ml), 2-tosyloxy-3-butyne (0.25 mole) is added and allowed to react for 3 hours at 70° C. After cooling, the reaction mixture is extracted with chloroform and the chloroform layer is washed and dried. Removal of the chloroform, in vacuo, yields crude 2-phthalimido-3-butyne.

(65%; m.p. 104.5°–106.5° C.).

c) Copper (I)-2-phthalimido-3-butynide

To a solution of copper sulfate pentahydrate (0.098 mol), under nitrogen, in 100 ml of 28% ammonium hydroxide and water (315 ml), hydroxylamine hydrochloride (0.175 mol) is added. After the change in color (blue to green) 62.5 ml of acetone is added. Immediately afterwards, a solution of 2-phthalimido-3-butyne (0.0875 mol) in 280 ml of acetone is added. After 5 minutes of vigorous stirring, a solution of 30.8 ml of glacial acetic acid in 455 ml of water is added. The yellow precipitate is filtered off, washed and dried in vacuo to yield the title product (yield 91%).

d) 2-Phthalimido-4-(p-cyanophenyl)-3-butyne

This reaction is carried out under a nitrogen stream. To 50 ml of dry pyridine, the product prepared in step (c) above (4.9 g) is added and p-iodobenzonitrile (20 mmol) is added. The reaction is refluxed for 15.5 hours. The product is then extracted with ether. The ether layers are washed and dried. Purification of the red oil obtained by flash chromatography yields the title product.

(m.p. 138°–142° C.; yield 44%)

e) 2-Amino-4-(p-cyanophenyl)-3-butyne hydrochloride

To a solution of the product prepared in step (d) above (1 mmol) in 20 ml ethanol, hydrazine (1.05 mmol of 97% solution) is added and the solution refluxed for 3.5 hours. The ethanol is evaporated and 20 ml of water is added. Then a 1N solution of NaOH is added dropwise to pH 12. The amine is extracted with ether and the ether is washed and dried. A solution of hydrogen chloride in ether is added to the solution and a yellow precipitate is produced. This is recrystallized to yield the title product.

(m.p. 200° C.; yield 89.5%)

EXAMPLE 3

2-Amino-3-butyne (formula (Ib) with R''$_1$=R''$_3$=R''$_4$=H, R''$_2$=CH$_3$)

a) 2-Tosyloxy-3-butyne

To a solution of tosyl chloride (0.5 mole) and commercial 3-butyn-2-ol (0.4 mole 40–50% aqueous solution) in ether (350 ml), potassium hydroxide (2.5 moles) is slowly added over a period of 15–30 minutes. The temperature is maintained at 0°–5° C. for the entire period and the reaction mixture is allowed to stand for 90 minutes. When the reaction is complete, the ether phase is washed and dried. Removal of the ether, in vacuo, yields crude 2-tosyloxy-3-butyne.

(m.p. 49°–51° C.; yield 95%).

b) 2-Phthalimido-3-butyne

To a solution of potassium phthalimide (0.275 mole; 5.1 g) in DMF (20 ml), 2-tosyloxy-3-butyne (0.25 mole) is added and allowed to react for 3 hours at 70° C. After cooling, the reaction mixture is extracted with chloroform and the chloroform layer is washed and dried. Removal of the chloroform, in vacuo, yields crude 2-phthalimido-3-butyne.

(3.4 g; m.p. 104.5°–106.5° C.).

c) 2-Amino-3-butyne hydrochloride

Hydrazine (1.05 mole of 97% solution) is added to a refluxing solution of recrystallized 2-phthalimido-3-butyne (0.1 mole) in methanol (150 ml). The reaction mixture is stirred over a period of 3.5 hours and the methanol is partly evaporated in vacuo. Water (100 ml) is added and dilute hydrochloric acid is added dropwise until the mixture attains pH 4. After stirring with gentle heating on a steam bath the rest of the methanol is removed, in vacuo. The solution is cooled and the phthalylhydrazide is filtered off. The aqueous solution is treated with activated charcoal, filtered and frozen. Removal of water by lyophillization yields of crude 2-amino-3-butyne hydrochloride.

(m.p. 166°–167° C.; yield 75%).

Other compounds of formulae (Ia) and (Ib) were prepared as described above, and their structure and melting point are reported in the following Tables:

TABLE 1

| | Formula (Ia) | | | | | |
|---|---|---|---|---|---|---|
| Ex. No. | R' | R'$_1$ | R'$_2$ | R'$_3$ | R'$_4$ | m.p.* (°C.) |
| 4 | m-CF$_3$ | H | H | CH$_3$ | CH$_3$ | 180-2 |
| 5 | m-CF$_3$ | H | H | CH$_3$ | Bn | 132-4 |
| 6 | H | H | H | n-C$_3$H$_7$ | n-C$_3$H$_7$ | 152-3 |
| 7 | m-CF$_3$ | H | CH$_3$ | CH$_3$ | CH$_3$ | 188-9 |
| 8 | m-CF$_3$ | H | H | n-C$_3$H$_7$ | n-C$_3$H$_7$ | 140-2 |
| 9 | m-CF$_3$ | H | H | H | CH$_2$—CH$_2$-φ | 212-3 |
| 10 | p-Cl | H | H | n-C$_3$H$_7$ | n-C$_3$H$_7$ | 141-2 |

TABLE 1-continued

Formula (Ia)

| Ex. No. | R' | R'$_1$ | R'$_2$ | R'$_3$ | R'$_4$ | m. p.* (°C.) |
|---|---|---|---|---|---|---|
| 11 | H | H | H | piperidine | | 228-30 |
| 12 | H | H | H | iso-C$_3$H$_7$ | iso-C$_3$H$_7$ | 131-2 |
| 13 | H | H | CH$_3$ | H | iso-C$_3$H$_7$ | 139-40 |
| 14 | m-CF$_3$ | H | H | iso-C$_3$H$_7$ | iso-C$_3$H$_7$ | 136-7 |
| 15 | m-CF$_3$ | H | H | H | 2-furyl | 184-5 |
| 16 | H | H | CH$_3$ | H | Bn | 185-6 |
| 17 | m-CF$_3$ | H | CH$_3$ | H | Bn | 172-3 |
| 18 | H | H | CH$_3$ | H | 2-furyl | 170-1 |
| 19 | m-CF$_3$ | H | CH$_3$ | H | 2-furyl | 143-4 |
| 20 | p-NO$_2$ | H | CH$_3$ | H | H | 211-2 |
| 21 | p-CON(CH$_3$)$_2$ | H | CH$_3$ | H | H | 207-8 |
| 22 | p-amido | H | CH$_3$ | H | H | 234-6 |
| 23 | p-OCH$_3$ | H | CH$_3$ | H | H | 183-4 |
| 24 | m-Cl | H | CH$_3$ | H | H | 194-5 |
| 25 | H | H | C$_2$H$_5$ | H | H | 185-6 |
| 26 | H | H | H | H | H | 216-7 |
| 27 | H | H | H | H | C$_2$H$_5$ | 179-80 |
| 28 | H | H | H | CH$_3$ | CH$_3$ | 161-2 |
| 29 | H | H | H | C$_2$H$_5$ | C$_2$H$_5$ | 136-7 |
| 30 | H | H | CH$_3$ | H | H | 178-9 |
| 31 | H | H | CH$_3$ | H | CH$_3$ | 150-1 |
| 32 | H | H | CH$_3$ | H | C$_2$H$_5$ | 179-80 |
| 33 | H | H | CH$_3$ | C$_2$H$_5$ | C$_2$H$_5$ | 135-6 |

*Values reported refer to the hydrochloride salts.

TABLE 2

Formula (Ib)

| Ex. No. | R''$_1$ | R''$_2$ | R''$_3$ | R''$_4$ | m. p.* (°C.) |
|---|---|---|---|---|---|
| 34 | H | CH$_3$ | CH$_3$ | H | 174-5 |
| 35 | H | CH$_3$ | CH$_3$ | CH$_3$ | 160-1 |
| 36 | CH$_3$ | CH$_3$ | H | H | 230-1 |

*Values reported refer to the hydrochloride salts.

PHARMACOLOGICAL EVALUATION

1. Inhibition of Isolation Induced Fighting Behavior in Mice

Young males CD #1 mice (15–20 g) are housed individually in white plastic cages (8×10×15 cm) for a period of 4 to 6 weeks. After this period of confinement, the animals usually develop a marked intraspecific aggressive behavior when they are placed in the same cage. Only the pairs of animals that exhibited a marked aggressive behavior (minimum of 10 bites starting in less than one minute and completed in less than 3 minutes) are selected for the experiment.

The compound to be studied is administered i.p. to the selected groups (N=8 pairs/dose×5 doses) and the aggressive behavior is tested again 30 minutes later. Only the pairs that did not bite each other at all over a period of 5 minutes are considered to be protected. The dose (mg/kg i.p.) that suppressed aggressive behavior in 50% of the animals (ED$_{50}$) is calculated by probit analysis. Chlorpromazine and diazepam are used as antipsychotic and anxiolytic standards, respectively. A one week washout period is allowed between treatments.

The effective doses against isolation induced aggressiveness (ED$_{50}$) of the compounds tested are reported in Table 3 hereinbelow.

2. Rotarod Neurotoxiciy Test in Mice

This test is performed in order to show any secondary effects on the central nervous system. Antipsychotics and anxiolytics cause problems with ataxia in animals. It is desirable that a product not cause problems with coordination at therapeutic levels.

Ataxia is measured according to the method of Dunham and Miya (1957). CD #1 mice (20–30 g) are used. Only the animals that are able to maintain their equilibrium on a rough surfaced rod (diameter: 3 cm) rotating at 6 r.p.m. for 2 minutes are used for the experiment.

The compound to be studied is administered i.p. (N=6/dose×4 doses) and the challenge is repeated 30 minutes later. Chlorpromazine and diazepam are used as antipsychotic and anxiolytic standards, respectively. The dose (mg/kg i.p.) causing the fall of 50% of the animals ($_{rot}$TD$_{50}$) is calculated by probit analysis.

The rotarod-neurotoxic doses ($_{rot}$TD$_{50}$) of the compounds tested are reported in Table 3 hereinbelow.

3. Acute Toxicity Test

CD #1 mice (20–30 g) are used for this test. The animals are individualy housed in glass beakers for a 2 hour period of acclimatization without food and water. After this period, the compound to be studied is administered i.p. (N=4–6/dose×2–6 doses).

The dose causing death of 50% of the animals (LD$_{50}$) is calculated by probit analysis.

The acute toxic doses (LD$_{50}$) of the compounds tested are reported in Table 3.

TABLE 3

| Compound No. | ED$_{50}$ | rot$^{TD}$50 | LD$_{50}$ |
|---|---|---|---|
| 1 | 12 | ≈65 | 130 |
| 2 | 8 | >100 | >100 |
| 3 | 8 | 720 | 1370 |
| 4 | 60 | 195 | 296 |
| 5 | 28 | 334 | 416 |
| 6 | 28 | 168 | 185 |
| 7 | 38 | 153 | 220 |
| 8 | 22 | ≧223 | 223 |
| 9 | 58 | 126 | 252 |
| 10 | 25 | 194 | 213 |
| 11 | 27 | 132 | 188 |
| 12 | 52 | ≧162 | 162 |
| 13 | 27 | ND | 120 |
| 14 | 24 | ND | ≈200 |
| 15 | 19 | 193 | 351 |
| 16 | 101 | 170 | 309 |
| 17 | 50 | 123 | 366 |
| 18 | 64 | ND | ≈300 |
| 19 | 73 | ND | ND |
| 20 | 10 | ≈120 | 152 |
| 21 | ND | ND | <100 |
| 22 | ND | ND | >100 |

TABLE 3-continued

| | | | |
|---|---|---|---|
| 23 | 24 | ND | >100 |
| 24 | ND | 50 | >100 |
| 25 | 16 | ≧84 | 84 |
| Compound N° | ED$_{50}$ | rot$^{TD}$$_{50}$ | LD$_{50}$ |
| 26 | ND | ND | ≧100 |
| 27 | 17 | 88 | 98 |
| 28 | 37 | ≧124 | 124 |
| 29 | 49 | ≧135 | 135 |
| 30 | 15 | ≈50 | 66 |
| 31 | 12 | ≧95 | 95 |
| 32 | 23 | ≧120 | 120 |
| 33 | 44 | ≧88 | 88 |
| 34 | 26 | ND | 828 |
| 35 | 92 | ND | ND |
| 36 | 176 | 391 | 779 |

As it is apparent from Tables 2 and 3, the propargylamine derivatives of the invention inhibit aggressive behavior in mice. Compound Nos 1, 2 and 3, i.e., 2-amino-4-(p-chlorophenyl)-3-butyne, 2-amino-4-(p-cyanophenyl)-3-butyne and 2-amino-3-butyne, are particularly potent inhibitors. Moreover, compound N° 3 is at least half as toxic as buspirone (LD$_{50}$=622 mg/kg p.o.).

The results of the rotarod neurotoxicity test show that, at low doses of the compounds of the invention, the animals are quiet, non-aggressive and yet exhibit unimpaired motor activity. In particular, compound N° 3 is much less neurotoxic than buspirone ($_{rot}$TD$_{50}$=135 mg/kg p.o.) and diazepam ($_{rot}$TD$_{50}$=13 mg/kg p.o. and 6 mg/kg i.p.). Thus, with compound N° 3, it is possible to administer higher dosages to a patient without the latter becoming confused or having problems with co-ordination.

There is also a marked difference of activity between the compounds of formula (I) that bear different substituents on the α-carbon atom (i.e. first carbon atom close to the amino group). This is an evidence that there might be a striking difference of activity among the compounds possessing a chiral center.

Compound N° 3 was submitted to the following additional pharmacological tests.

4. Inhibition of Spontaneous Motor Activity in Mice

Female CD #1 mice (20–30 g) are used for this experiment. The effect of the compound to be studied on spontaneous activity was evaluated by an automated DIGISCAN XYZ system. This system allows the simultaneous quantification of the following parameters:
  horizontal activity;
  vertical activity;
  total distance;
  movement time;
  rest time;
  stereotypy time;
  number of stereotypic movements;
  number of movements;
  number of vertical movements;
  number of clockwise revolutions; and
  number of counterclockwise revolutions.

Two animals are studied simultaneously, one treated and one control. After a 2 hour period of acclimatization to the room, a first activity count of 10 minutes duration is perfomed. The compound to be studied is then administered i.p. and the spontaneous activity is reevaluated 30 minutes later over a period of 10 minutes. The dose causing a reduction of 50% of the evaluated motor activity (ED$_{50}$) is calculated by probit analysis.

The results obtained with compound N° 3 in comparison with buspirone are reported in the following Table:

TABLE 4

| | Compound No 3 | Buspirone |
|---|---|---|
| Horizontal activity | 4.3 ± 2.2 mg/kg ($r^2$ = 0.8585) | 20.5 ± 16.7 mg/kg ($r^2$ = 0.9974) |
| Vertical activity | 2.5 ± 1.2 mg/kg ($r^2$ = 0.8270) | no dose-response relationship |
| Total distance | 5.5 ± 3.4 mg/kg ($r^2$ = 0.8009) | 22.6 ± 15.8 mg/kg ($r^2$ = 0.9263) |
| Movement time | 8.1 ± 4.5 mg/kg ($r^2$ = 0.8783) | 19.9 ± 8.9 mg/kg ($r^2$ = 0.9720) |
| Number of movements | 11.8 ± 5.9 mg/kg ($r^2$ = 0.8662) | no dose-response relationship |
| Vertical time | 2.6 ± 1.5 mg/kg ($r^2$ = 0.7026) | no dose-response relationship |
| Vertical movements | 3.2 ± 1.6 mg/kg ($r^2$ = 0.8525) | no dose-response relationship |
| Stereotypy time | 3.8 ± 1.6 mg/kg ($r^2$ = 0.9107) | 22.7 ± 13.7 mg/kg ($r^2$ = 0.9924) |
| Number of stereotypic movements | 5.5 ± 2.2 mg/kg ($r^2$ = 0.9546) | no dose-response relationship |
| Clockwise revolutions | 3.3 ± 1.6 mg/kg ($r^2$ = 0.8686) | 17.9 ± 6.9 mg/kg ($r^2$ = 0.9997) |
| Counterclockwise revolutions | 2.7 ± 1.9 mg/kg ($r^2$ = 0.6531) | no dose-response relationship |

5. Inhibition of Spontaneous Motor Activity in Rats

The method is the same as described above for mice, except that because of the size of the animals (Sprague Dawley rats; 300 g), the test and control animals are not evaluated simultaneously, but alternatively.

The results obtained with compound N° 3 in comparison with buspirone are reported in the following Table:

TABLE 5

| | Compound No 3 | Buspirone |
|---|---|---|
| Horizontal activity | 4.2 ± 1.8 mg/kg ($r^2$ = 0.8856) | 2.7 ± 0.8 mg/kg ($r^2$ = 0.9968) |
| Total distance | 4.9 ± 2.0 mg/kg ($r^2$ = 0.9823) | 2.8 ± 0.7 mg/kg ($r^2$ = 0.9987) |
| Movement time | 5.5 ± 2.3 mg/kg ($r^2$ = 0.9255) | 3.2 ± 0.6 mg/kg ($r^2$ = 0.9989) |
| Number of movements | 11.8 ± 7.9 mg/kg ($r^2$ = 0.2080) | 5.3 ± 0.9 mg/kg ($r^2$ = 1.0000) |
| Stereotypy time | 4.2 ± 1.7 mg/kg ($r^2$ = 0.5804) | 1.7 ± 0.6 mg/kg ($r^2$ = 0.9956) |
| Number of stereotypic movements | 5.2 ± 2.4 mg/kg ($r^2$ = 0.6848) | 3.1 ± 0.8 mg/kg ($r^2$ = 0.9919) |
| Clockwise revolutions | 4.1 ± 1.4 mg/kg ($r^2$ = 0.8097) | 2.3 ± 0.9 mg/kg ($r^2$ = 0.9893) |
| Counterclockwise revolutions | 3.7 ± 1.7 mg/kg ($r^2$ = 0.8699) | 2.9 ± 0.7 mg/kg ($r^2$ = 0.9836) |

As it is apparent from Tables 4 and 5, both compound N° 3 and buspirone inhibit spontaneous motor activity in mice and rats. Compound N° 3 is more active than buspirone in mice and of comparable activity in rats. This activity can be associated with the "taming" effect in animals. Anxiolytics and antipsychotics have such an effect.

6. Inhibition of Conditioned Avoidance Response in Rats

Male Sprague Dawley rats (200–250 g) are trained to avoid an electric foot shock, by continuously changing room with the appropriate visuals and auditory signals, in an automatic 2-way conditioned avoidance apparatus (Coulbourn Instrument Co.). Only the animals that perform at least a 70% avoidance (3 successive training sessions) are kept for the experiment.

The day of the experiment, the selected animals are submitted to a pre-treatment control session. The compound to be studied is then administered i.p. and the animals are placed back in the apparatus for evaluation 30 minutes later. Diazepam was used as a standard.

The results obtained with compound N° 3 in comparison with buspirone and diazepam are reported in the following Table:

TABLE 6

| Compound No 3 | Buspirone | Diazepam |
|---|---|---|
| very active at first exposure (3% at 10 mg/kg i.p.) | 48 mg/kg p.o. | 57.5% at 5 mg/kg i.p. |
| much less active if re-exposed (29% at 10 mg/kg i.p.) | | |
| $ED_{50}$ = 21.5 ± 11.2 mg/kg i.p. ($r^2$ = 0.43) calculated with repeated exposure | | |

Both compound N° 3 and buspirone inhibit conditioned avoidance in rats, but are less active than diazepam. There is a loss of activity in the case of compound N° 3 after the first exposure to the drug.

This experiment is commonly used to screen tranquilizing drugs, the end-point of the experiment being the loss of alertness. This test thus demonstrates that compound N° 3 does not seem to impair the animal's sensory discrimination at doses 2 to 3 times above that which produces a quieting effect with repeated exposure.

7. Potentiation of Sleeping Time Induced by Ethanol in Mice

This test was done with male CD #1 mice of 25-35 g. The mice are injected intraperitoneally (8 mice per dose). A subhypnotic dose of ethanol (12 ml/kg of 50% ethanol solution) is administered orally 30 minutes later.

The loss of the righting reflex is evaluated, for each animal, 30 minutes after the administration of the alcohol. It is considered that there is a potentialization of ethanol narcosis if the righting time exceeded 30 seconds.

The results which are reported in Table 7 are expressed in terms of the percentage of animals displaying a loss of the righting reflex versus the administered dose. Chlorpromazine (5 mg/kg i.p.) is used as a standard.

TABLE 7

| Compound No 3 | Buspirone | Chlor-promazine |
|---|---|---|
| active at t = 30 min. 50% at 10 and 30 mg/kg i.p. 25% at 100 mg/kg i.p. | 62.8 mg/kg p.o. | 100% at 5 mg/kg i.p. |

Both compound N° 3 and buspirone potentiate the effect of a subhypnotic effect dose of ethanol. In this potentiation, buspirone is more effective than compound N° 3.

The activity in this test is associated with a sedative depressant effect on the central nervous system. The interaction of antipsychotic and anxiolytic agents with ethanol is well known. However, it is interesting to note that clinically and at therapeutic doses, buspirone does not appear to potentiate the effects of ethanol. The minimal effect of buspirone observed in this test appears to confirm this fact. It thus appears that compound N° 3 will have little interaction with ethanol.

8. Inhibition of Exploratory Behavior in Rats (Hole Poking).

This test is done with Sprague-Dawley male rats of about 300 g. Activity is evaluated with a DIGISCAN XYZ activity cage connected to a DIGISCAN ANALYSER DCM-4. A perforated plate (16 holes of 2-5 cm diameter) is placed in the enclosure and on the activity case to register vertical activity. The number of times the rat placed his snout into the holes during a 10 minute period is recorded. The test was started 30 minutes after the interperitoneal injection of the compound to be studied.

The results which are reported in Table 8 are expressed in terms of the dose required to diminish by 50% the exploratory behavior, with reference to animals injected with the carrier only. Diazepam and buspirone are used as standards.

TABLE 8

| Compound No 3 | Buspirone | Diazepam |
|---|---|---|
| 4.6 ± 2.6 mg/kg i.p. | 2.8 ± 0.6 mg/kg i.p. | 14.2 ± 5.0 mg/kg i.p. |

Both compound N° 3 and buspirone tend to inhibit exploratory behavior in rats after the first administration. Their activity is comparable. It is interesting to note that they are more potent, in this respect, than diazepam but they rapidly lose their ability to produce this effect after the first administration, which is not the case with diazepam.

9. Effect on Body Temperature in Mice

Female CD #1 mice (20–30 g) are used. Rectal temperature is recorded before and one hour after s.c. administration of the compound to be studied (N=8/doses×4 doses). The solvent used is sterile water for intravenous injection.

The results which are reported in Table 9 are expressed in terms of the variation of temperature for different doses. Buspirone was tested on Sprague Dawley rats.

TABLE 9

| | Temp. Difference from Control | |
|---|---|---|
| Dose | Compound No 3 | Buspirone |
| 10 | −2.6 | −2.7 |
| 30 | −2.5 | −3.6 |
| 100 | −4.1 | −5.8 |

Compound N° 3 induced a slight, transient hypothermia comparable to that induced by buspirone. It is to be noted that hypothermia is generally associated with antipsychotic activity.

10. Relationship between the Plasma Concentration of Compound N° 3 and the Inhibition of Aggressive Behavior in Combative Mice A. Method of Evaluation A calibration curve is established using mouse blood plasma. Two samples are used for each concentration. The method used is as follows.

200 μl of plasma are taken and denaturated with 400 μl of acetonitrile. 500 μl of the clear liquid is taken.

A derivative is made with 50 μl of orthophthalaldehyde (0.05M) in a test tube and 25 μl of the solution is injected into a high performance liquid chromatography apparatus after 30 minutes.

The plasma solutions are prepared as shown in Table 10. 3-Amino-4-pentyne is used as standard.

TABLE 10

| μl Compound No 3 ($10^{-3}$ M) | μl Compound No 3 ($5 \times 10^{-4}$ M) | μl Standard ($10^{-3}$ M) | μl Plasma | Conc. ($10^{-5}$ M) |
| --- | --- | --- | --- | --- |
| — | 5 | 10 | 185 | 1.25 |
| — | 10 | 10 | 180 | 2.50 |
| 10 | — | 10 | 180 | 5.00 |
| 15 | — | 10 | 175 | 7.50 |

The experimental results are shown in the following Table:

TABLE 11

| Conc. ($10^{-5}$ M) | Integration Comp. No 3 Integration Standard | Integration Comp. No 3 Integration Standard |
| --- | --- | --- |
| 1.25 | 0.2153 | 0.2351 |
| 2.50 | 0.5711 | 0.5218 |
| 5.00 | 1.2050 | 1.1639 |
| 7.50 | 1.7245 | 1.8519 |

The following equation describes the calibration curve:

Integration ratio $= (0.250 \times$ conc.$) - 0.081$  $r^2 = 0.9981$ (N=8)

The concentration of compound N° 3 in the plasma is given by the following equation:

$$\text{Conc.} = \frac{\text{Integration ratio} + 0.081}{2.5 \times 10^{-4} \text{ 1/Mol}}$$

B. Evaluation in Vivo

The pharmacokinetic profile is established in combative mice.

In order to determine the ability of compound N° 3 to inhibit combativity in mice, a dose of 10 mg/kg i.p. of the substance is administered to 30 combative mice using the same criterion as described above for evaluating the inhibition of isolation induced fighting behavior in mice.

The mice are placed together, in pairs, for 5 minutes. This pairing is performed 10, 25, 55, 85 and 115 minutes after the administration of compound N° 3. One minute after each of the 5 minute periods of placing the animals together, three pairs of animals are anesthetized with ether and guillotined in order to determine the concentration of compound N° 3 in the plasma. The plasma sample is prepared by centrifugation (16,000 G) of 800 μl of blood to which 50 μl of EDTA Na$_4$ (0.1M) is added. The inhibition of aggressive behavior at the different times in which the animals are placed together and the number of pairs evaluated is shown in the following Table:

TABLE 12

| Time (min.) | Number of pairs evaluated |
| --- | --- |
| 15 | 15 |
| 30 | 12 |
| 60 | 9 |
| 90 | 3 |
| 120 | 3 | c. Plasma Concentration of Compound N° 3 as a Function of Time

The plasma concentrations of compound N° 3 determined as a function of time after the administration of a dose of 10 mg/kg i.p. are shown in the following Table:

TABLE 13

| Time (min.) | N | Concentration ± S.E. ($\times 10^{-4}$ M) |
| --- | --- | --- |
| 15 | 6 | 48 ± 4 |
| 30 | 6 | 20 ± 2 |
| 60 | 5 | 9 ± 2 |
| 90 | 6 | N.D. |
| 120 | 6 | N.D. |

N.D.: Not detectable ($<5 \times 10^{-6}$ M)
S.E.: Standard Error (S/$\sqrt{N}$)

FIG. 1 shows that the elimination of compound N° 3 is very rapid. Compound N° 3 was not detectable, by the method used, 90 minutes after the injection of a dose of 10 mg/kg i.p.

D. Correlation of Plasma Concentration of Compound N° 3 and the Inhibition of Aggressive Behavior The percentage of inhibition observed at various times is shown in the following Table:

TABLE 14

| Time (min.) | N (pairs) | Inhibition (%) |
| --- | --- | --- |
| 15 | 15 | 75 |
| 30 | 12 | 87.5 |
| 60 | 9 | 100 |
| 90 | 3 | 100 |
| 120 | 3 | 100 |

As it is apparent from Table 14, compound N° 3 exhibits noticeable activity after a few minutes and maximum activity after 60 minutes.

FIG. 1 illustrates the relationship between the plasma concentration of compound N° 3 and its effect on inhibiting aggressive behavior. It is to be noted that its activity is maximal when the plasma concentration is no longer detectable by the method used in the determinations (limit $5 \times 10^{-6}$ M or 0.35 μg/ml).

11. Duration of Antiaggressive Effect

The method used is the same as described above for evaluating the inhibition of isolation induced fighting behavior in mice, except that a single dose (10 mg/kg i.p.; N=8) is administered and the animals are evaluated every 30 minutes for a period of 5.5 hours.

As shown in FIG. 2, the inhibitory effect that compound N° 3 has on the aggressive behavior of combative mice is sustained for approximately 4 hours.

12. Persistence of Antiaggressive Effect

The method used is the same as described above for evaluating the inhibition of isolation induced fighting behavior in mice, except that a single dose (10 mg/kg i.p.; N=16) is administered daily for a period of five days and the animals are evaluated every day.

FIG. 3 illustrates that the inhibitory effect which compound N° 3 has on the aggressive behavior of combative mice also persists when the compound is administered on a daily basis.

We claim:

1. A method of treating anxiety, psychotic states and aggressive behavior in an affected animal, which method comprises administering to said animal a nontoxic, anxiolytic or antipsychotic effective dose of a propargylamine derivative having the general formula:

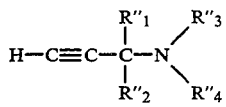

wherein:
  $R''_1$ is a hydrogen atom, or a lower alkyl group;
  $R''_2$ is a lower alkyl group; and
  $R''_3$ and $R''_4$ are the same or different and each represent a hydrogen atom or a lower alkyl group; or
a pharmaceutically acceptable acid addition salt thereof, said non-toxic, anxiolytic or antipsychotic effective dose producing in said animal an anti-aggressive behavior in the substantial absence of impaired motor activity.

2. A method as claimed in claim 1, wherein a unit dose of about 30 to about 500 mg of said propargylamine derivative of formula (Ib) or a pharmaceutically acceptable acid addition salt thereof is administered.

3. A method as claimed in claim 1, wherein said propargylamine derivative of formula (Ib) is 2-amino-3-butyne.

4. The method of claim 1, wherein the propargylamine derivative administered is a derivative of formula (Ib) in which $R''_1$ is a hydrogen atom, $R''_2$ and $R''_3$ each represent a methyl group and $R''_4$ is a hydrogen atom or a methyl group, or a pharmaceutically acceptable acid addition salt thereof.

5. The method of claim 1 wherein $R''_1$ is a hydrogen atom.

6. The method of claim 1 wherein $R''_1$ is a lower alkyl group.

7. The method of claim 1 wherein $R''_3$ and $R''_4$ are the same.

8. The method of claim 7 wherein $R''_3$ and $R''_4$ are hydrogen.

9. The method of claim 7 wherein $R''_3$ and $R''_4$ are lower alkyl.

10. The method of claim 5 wherein $R''_3$ and $R''_4$ are the same.

11. The method of claim 5 wherein $R''_3$ and $R''_4$ are different.

12. A method as claimed in claim 3, wherein a unit dose of about 30 to about 500 mg of 2-amino-3-butyne in a pharmaceutically acceptable carrier is administered.

13. A method as claimed in claim 12, wherein said unit dose is administered approximately every 4 hours.

* * * * *

UNITED STATES PATENT AND TRADEMARK OFFICE
CERTIFICATE OF CORRECTION

PATENT NO. : 5,436,273
DATED : Jul. 25, 1995
INVENTOR(S) : Romano Salvador, David Z. Simon, Louis Leonard It is certified that error appears in the above-indentified patent and that said Letters Patent is hereby corrected as shown below:

On title page, item [73],

Delete

"Lowchol Scientific, Inc.
         Frelighsburg Ontario J0J 130
        CANADA"

and insert

-- UNIVERSITE DE MONTREAL
           2900 Edouard - Montepetit
           Montreal, Quebec
           CANADA   H3C 3J7 --.

Signed and Sealed this

Twenty-fifth Day of June, 1996

*Attest:*

BRUCE LEHMAN

*Attesting Officer*     *Commissioner of Patents and Trademarks*